(12) United States Patent
Cao et al.

(10) Patent No.: US 8,911,943 B2
(45) Date of Patent: Dec. 16, 2014

(54) HIGH THROUGH-PUT ANALYSIS OF TRANSGENE BORDERS

(75) Inventors: Zehui Cao, Westfield, IN (US); Stephen Novak, Westfield, IN (US); Ning Zhou, Zionsville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 140 days.

(21) Appl. No.: 13/439,933

(22) Filed: Apr. 5, 2012

(65) Prior Publication Data

US 2012/0258867 A1    Oct. 11, 2012

Related U.S. Application Data

(60) Provisional application No. 61/471,833, filed on Apr. 5, 2011.

(51) Int. Cl.
*C12Q 1/68* (2006.01)

(52) U.S. Cl.
CPC ............ *C12Q 1/6858* (2013.01); *C12Q 1/6895* (2013.01)
USPC ....................................................... 435/6.11

(58) Field of Classification Search
None
See application file for complete search history.

(56) References Cited

U.S. PATENT DOCUMENTS

| | | | |
|---|---|---|---|
| 5,565,340 A | 10/1996 | Chenchik et al. | |
| 5,759,822 A | 6/1998 | Chenchik et al. | |
| 6,514,706 B1 * | 2/2003 | Von Kalle et al. | 435/6.12 |
| 2003/0233670 A1 | 12/2003 | Edgerton et al. | |
| 2007/0037139 A1 | 2/2007 | Tomono et al. | |

FOREIGN PATENT DOCUMENTS

WO    WO03052073    *    6/2003    .............. C12P 19/34

OTHER PUBLICATIONS

Nielsen et al. (Eur Food Res Technol, 2008, 226:949-956; IDS reference).*
Ingham et al. (Biotechniques, 2001, 31:132-140).*
Harkey, M. A. et al. "Multiarm High-Throughput Integration Site Detection: Limitations of LAM-PCR Technology and Optimization for Clonal Analysis" *Stem Cells and Development*, 2007, pp. 381-392, vol. 16.
Nguyen, T. N. et al. "Chromosomal sequencing using a PCR-based biotin-capture method allowed isolation of the complete gene for the outer membrane protein A of *Klebsiella pneumoniae*" *Gene*, 1998, pp. 93-101, vol. 210.
Nielsen, C. R. et al. "Anchored PCR for possible detection and characterisation of foreign integrated DNA at near single molecule level" *Eur. Food Res. Technol.*, 2008, pp. 949-956, vol. 226.
Silver, J. et al. "Novel Use of Polymerase Chain Reaction to Amplify Cellular DNA Adjacent to an Integrated Provirus" *Journal of Virology*, May 1989, pp. 1924-1928, vol. 63, No. 5.
Zhang, X. et al. "Single-stranded DNA ligation by T4 RNA ligase for PCR cloning of 5'-noncoding fragments and coding sequence of a specific gene" *Nucleic Acids Research*, 1996, pp. 990-991, vol. 24, No. 5.
Written Opinion in International Application No. PCT/US2012/31334, Aug. 10, 2012, pp. 1-6.

* cited by examiner

*Primary Examiner* — Stephanie K Mummert
(74) *Attorney, Agent, or Firm* — Ronald S. Maciak; Saliwanchik, Lloyd & Eisenschenk

(57) ABSTRACT

The present invention is a method to identify unknown DNA sequences which flank known DNA sequences. The invention improves the accuracy, sensitivity, and reproducibility for determining unknown DNA sequences which flank a known DNA sequence. This claimed method can be deployed as a high throughput method to quickly and efficiently identify plant genomic chromosomal sequences which flank a transgene. Further analysis of these unknown sequences can be used to characterize the transgene insertion site for the identification of rearrangements, insertions and deletions which result from the integration of the transgene. In addition, analysis of the chromosomal flanking sequences can be used to identify the location of the transgene on the chromosome.

22 Claims, No Drawings

HIGH THROUGH-PUT ANALYSIS OF TRANSGENE BORDERS

CROSS-REFERENCE TO RELATED APPLICATION

This application claims the benefit of U.S. Provisional Application Ser. No. 61/471,833, filed Apr. 5, 2011, the disclosure of which is hereby incorporated by reference in its entirety, including all figures, tables and amino acid or nucleic acid sequences.

TECHNICAL FIELD OF THE INVENTION

The subject invention relates generally to the fields of plant molecular biology and biochemistry. The subject invention concerns a modified Polymerase Chain Reaction (PCR) method for analyzing a transgene border and the determining the chromosomal sequence which flanks the transgene.

BACKGROUND OF THE INVENTION

Determining the genomic location and the chromosomal flanking sequence adjacent to an inserted transgene is technically challenging. Various methods have been developed to overcome the limitation of identifying the unknown DNA sequences which flank a known DNA sequence. However, these traditional PCR methods for the identification or genomic chromosomal sequences which flank a known transgene such as LM-PCR (also described as Genome Walking) and other methods including: inverse PCR (i-PCR), thermal asymmetric interlaced PCR (TAIL-PCR), anchored PCR (a-PCR) and randomly primed PCR (rm-PCR) are hindered by low detection sensitivity (requiring large quantities of template DNA) or low specificity because of losses of DNA during preparation.

The polymerase chain reaction (PCR) is a commonly employed molecular biology method. The method is performed by denaturing double-stranded template DNA, annealing oligonucleotide primers to the DNA template, and extension of a DNA strand via a DNA polymerase. The oligonucleotide primers are designed to anneal to opposite strands of the DNA and positioned so that the DNA strand produced by the DNA polymerase serves as a template strand for the other primer. Each cycle is repeated, resulting in the exponential amplification of a DNA fragment. (Mullis et al., U.S. Pat. Nos. 4,683,195, 4,683,202, and 4,800,159). The use of PCR by those skilled in the art is fundamental for amplifying and isolating DNA fragments for subsequent analysis.

Isolation and analysis of DNA templates via the polymerase chain reaction (PCR) requires knowledge of the flanking DNA sequences. Unfortunately, this requirement limits PCR amplification to regions of known DNA sequence. The use of PCR methodologies to identify the location of a transgene location within a genome is hindered by the random insertion of the transgene into an unknown chromosomal location within the genome of an organism. Methods to identify unknown DNA sequences which are located adjacent to a known DNA sequence are necessary for the identification of a transgene location within the chromosome of an organism. In addition such methods can be used to identify novel gene sequences to identify new traits, to determine the genomic location of a transposon or viral sequence which has been inserted into the genome of an organism, or to identify the chromosomal location of polynucleotide sequences inserted into the genome via insertion mutagenesis.

Various methods have been developed to overcome the limitation of the unknown DNA sequences which flank a known DNA sequence. A Ligation Mediated PCR (LM PCR) method wherein a genomic library is generated and adapters are annealed to DNA fragments for PCR amplification is marketed as the GENOME WALKER UNIVERSAL KIT™ (see U.S. Pat. No. 5,565,340, and U.S. Pat. No. 5,759,822). Another method commonly used is the inverse PCR reaction (see Silver and Keerikatte (1989), J. Virol., 63:1924-1928), wherein DNA is digested with a restriction enzyme and self ligated resulting in a contiguous circle. PCR amplification using oligonucleotide primers which bind to known sequences results in amplification and elucidation of the unknown flanking sequences. Unfortunately these methods are inefficient and time consuming. These and other traditional PCR methods (including thermal asymmetric interlaced PCR [TAIL-PCR], anchored PCR [a-PCR] and randomly primed PCR [rm-PCR]) are hindered by low detection sensitivity (requiring large quantities of template DNA) or low specificity because of losses of DNA during preparation.

The development of a method which can improve detection sensitivity by purifying chromosomal DNA fragments which contain both the known and unknown DNA sequences can result in a sensitive method for detecting and characterizing unknown DNA regions which are located adjacent to a known DNA sequence. The development of the Linear Amplification Mediated Polymerase Chain Reaction (LAM PCR) method achieves these goals. see U.S. Pat. No. 6,514,706. The LAM PCR method is particularly suited to amplify and analyze DNA fragments, the sequence of which is only known in part.

The development of a method which can improve detection sensitivity by purifying chromosomal DNA fragments which contain both the known and unknown DNA sequences can result in a sensitive method for detecting and characterizing unknown DNA regions which are located adjacent to a known DNA sequence. The development of the LAM PCR method achieves these goals. LAM PCR is a modified PCR method that is used for analyzing unknown chromosomal flanking sequences located adjacent to a known DNA sequence. The LAM PCR method can be used to identify and/or sequence an unknown DNA or RNA sequence flanking a known DNA or RNA region.

The LAM PCR method consists of the following steps. A primer extension reaction is performed using a chromosomal DNA as a template and an oligonucleotide primer which binds to a known DNA sequence within the chromosomal DNA. The oligonucleotide primer is complementary to a long terminal repeat (LTR) sequence, which is a sequence characteristic of a retrovirus, and labeled with biotin at the end of the oligonucleotide primer. The single-stranded DNA product of the linear PCR is bound to magnetic beads having immobilized streptavidin. This step serves to isolate the single-stranded amplified DNA fragment containing the known LTR sequence and an unknown sequence derived from the chromosome. The single-stranded DNA is converted into a double-stranded DNA by synthesizing the complementary strand. The double-stranded DNA is cleaved with a restriction enzyme that recognizes a sequence and cleaves the double-stranded DNA at the sequence. A double-stranded DNA called a linker cassette is ligated to the terminus. Subsequent PCR reactions are conducted using the thus obtained ligation product as a template as well as a primer complementary to the LTR and a primer complementary to the linker cassette. A DNA fragment that contains the LTR and chromosome DNA flanking sequence adjacent to the LTR is amplified. As a result the previously unknown retrovirus integration site can be determined.

The LAM PCR method is currently considered to be an effective system for analyzing unknown DNA sequences adjacent to a known DNA sequence. Modifications and improvements to the LAM PCR method have been described in the art. see U.S. Pat. App. US2007/0037139 and Harkey et al., (2007) *Stem Cells Dev.*, June; 16(3): 381-392.

The LAM PCR method was modified in U.S. Pat. App. US2007/0037139 to improve the detection of a biological sample having a retrovirus integrated at various sites. The reaction conditions of the traditional LAM PCR method produced results that did not reflect the actual state of clones existing in the cell population of the sample. A modification was developed in which more integration fragments were PCR amplified without being biased toward a fragment amplified from a specific clone. The modification to the LAM PCR method allowed researchers to determine the extent of cells having an integrated gene in the population and to determine the ratio of a specific cell in the population.

In addition, Harkey et al., (2007) describe an optimized, multi-arm, high throughput modification of the LAM PCR method wherein the detection capacity was improved 90% with exhaustive sampling. The modified protocol facilitated accurate estimates of the total pool size, thus providing a rapid, cost-effective approach for generating large insertion-site data of preferred genomic locations for vector integration.

The subject invention describes a further significant modification and solves several traditional LAM-PCR problems by eliminating the steps of generating a double stranded DNA fragment then digesting the double stranded DNA fragment and denaturing the double stranded DNA fragment.

BRIEF SUMMARY OF THE INVENTION

The subject invention provides a method for finding an unknown polynucleotide sequence adjacent to a known polynucleotide sequence in isolated plant DNA, which comprises digesting the isolated plant DNA that contains a portion or all of the known polynucleotide sequence and an adjacent unknown polynucleotide sequence with one or more suitable restriction enzymes to produce a plurality of digested polynucleotide restriction fragments; synthesizing a complementary strand of the digested polynucleotide restriction fragments using an oligonucleotide primer sequence having an attachment chemistry bound to the 5' end of the oligonucleotide primer sequence; isolating the complementary strand by binding the attachment chemistry to a suitable isolation matrix, then denaturing the complementary strand from the digested polynucleotide restriction fragments; ligating a single stranded adapter to the isolated complementary strand bound to the isolation matrix to produce a ligated isolated complementary strand; performing a first PCR amplification of the ligated isolated complementary strand using a first PCR primer designed to bind to the known polynucleotide sequence and a second PCR primer designed to bind to the single stranded adapter to produce a first PCR amplicon; performing a second PCR amplification of said first PCR amplicon, wherein the second PCR amplification amplifies an internal sequence of said first PCR amplicon to produce a second PCR amplicon; and sequencing the second PCR amplicon to ascertain the sequence of the unknown polynucleotide sequence.

An embodiment of the subject invention, disclosed herein, is a method for the isolation and identification of transgene border sequences. An embodiment of the subject invention is a method which is readily applicable for high throughput applications to determine the transgenic copy number and the chromosomal location of a genomic insertion site. In addition, the subject invention can be used for the simultaneous detection of multiple insertion sites within one reaction. The subject invention discloses a method which has improved sensitivity and specificity for the detection of unknown polynucleotide fragments which flank a known polynucleotide fragment. Moreover, the subject invention can be deployed to detect the unknown DNA sequences which are located adjacent to any target sequence, including viral sequences and insertional mutagenesis sites created via transposon mutagenesis or mutagenesis generated via T-strand integration.

An embodiment of the subject invention relates in part to transgenic event identification using such flanking, junction, and insert sequences. According to the subject invention, a modified PCR analysis and DNA sequencing analysis methods using amplicons that span across inserted transgene DNA and its borders can be used to detect or identify commercialized transgenic plant varieties or lines derived from the proprietary transgenic plant lines.

The transgene border and adjacent chromosomal flanking sequences of the subject invention are diagnostic for a transgenic event. Based on these sequences, transgenic plant lines can be identified in different plant genotypes by analysis of the chromosomal flanking and transgene sequences. Thus, an embodiment of the subject invention describes a method that can be used to identify transgenic plant lines.

The chromosomal flanking sequences of the subject invention are especially useful in conjunction with plant breeding, to determine which progeny plants comprise a given event, after a parent plant comprising an event of interest is crossed with another plant line in an effort to impart one or more additional traits of interest in the progeny. An embodiment of the subject invention is the determination of the chromosomal flanking/junction sequences to benefit breeding programs as well as quality control, especially for commercialized transgenic plant lines.

Furthermore, the identification of chromosomal flanking sequences can be used to specifically identify the genomic location of each transgenic insert. This information can be used to develop molecular marker systems specific for each event. These molecular marker systems can be used for accelerated breeding strategies and to establish linkage data. An embodiment of the subject invention are molecular marker systems.

Still further, the chromosomal flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS (matrix attachment regions), and the like).

The methods of this invention can be used to obtain and ascertain the sequence of the unknown polynucleotide from a transgenic organism. In any of the methods of this invention, the sample can be genomic DNA and the transgenic organism can be a transgenic plant. Transgenic plants analyzed by any of the methods of this invention can be selected from plants consisting of barley, corn, oat, sorghum, turf grass, sugarcane, wheat, alfalfa, banana, broccoli, bean, cabbage, canola, carrot, cassava, cauliflower, celery, citrus, cotton, a cucurbit, eucalyptus, flax, garlic, grape, onion, lettuce, pea, peanut, pepper, potato, poplar, pine, rye, rice, sunflower, safflower, soybean, strawberry, sugar beet, sweet potato, tobacco, tomato, ornamental, shrub, nut, millet, and pasture grass.

The methods of this invention can be used to obtain and ascertain the sequence of the unknown polynucleotide from a non-transgenic organism. In any of the methods of this invention, the sample can be genomic DNA and the non-transgenic organism can be a plant. Plants analyzed by any of the methods of this invention can be selected from plants consisting of barley, corn, oat, sorghum, turf grass, sugarcane, wheat, alfalfa, banana, broccoli, bean, cabbage, canola, carrot, cassava, cauliflower, celery, citrus, cotton, a cucurbit, eucalyptus, flax, garlic, grape, onion, lettuce, pea, peanut, pepper, potato, poplar, pine, rye, rice, sunflower, safflower, soybean, strawberry, sugar beet, sweet potato, tobacco, tomato, ornamental, shrub, nut, millet, and pasture grass. In any of the methods of the invention, the unknown polynucleotide sequence adjacent to a known polynucleotide sequence can be a native polynucleotide of agronomic interest.

BRIEF DESCRIPTION OF THE SEQUENCES

SEQ ID NO:1 describes the 5' biotinylated primer labeled as 4468-3PA01-2Btn.
SEQ ID NO:2 describes the 5' phosphorylated adapter labeled as ZC-Adp-01.
SEQ ID NO:3 describes the primer labeled as PAT-InvPriF.
SEQ ID NO:4 describes the primer labeled as Zn_Adt_PCR_01.

DETAILED DESCRIPTION OF THE INVENTION

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The terms "nucleic acid," "polynucleotide," "polynucleotide sequence," and "nucleotide sequence" are used to refer to a polymer of nucleotides (A,C,T,U,G, etc. or naturally occurring or artificial nucleotide analogues), e.g., DNA or RNA, or a representation thereof, e.g., a character string, etc. depending on the relevant context. The terms "nucleic acid" and "polynucleotide" are used interchangeably herein; these terms are used in reference to DNA, RNA, or other novel nucleic acid molecules of the invention, unless otherwise stated or clearly contradicted by context. A given polynucleotide or complementary polynucleotide can be determined from any specified nucleotide sequence. A nucleic acid may be in single- or double-stranded form.

The term "isolated," refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

The term "plant," includes plants and plant parts including but not limited to plant cells and plant tissues such as leaves, stems, roots, flowers, pollen, and seeds. The class of plants that can be used in the present invention is generally as broad as the class of higher and lower plants amenable to mutagenesis including angiosperms (monocotyledonous and dicotyledonous plants), gymnosperms, ferns and multicellular algae.

The term "promoter," typically refers to a DNA sequence which directs the transcription of a structural gene to produce RNA. Typically, a promoter is located in a region 500 base pairs upstream of a gene, proximal to the transcription start site. If a promoter is an inducible promoter, then the rate of transcription increases or decreases in response to an exogenous or endogenous inducing agent. In contrast, the rate of transcription is regulated to a lesser degree by an inducing agent if the promoter is a constitutive promoter.

The term "transgenic plant," refers to a plant or progeny thereof derived from a transformed plant cell or protoplast, wherein the plant DNA contains an introduced exogenous DNA molecule not originally present in a native, non-transgenic plant of the same.

The term "vector," as used herein refers to any recombinant polynucleotide construct that may be used for the purpose of transformation, i.e., the introduction of heterologous DNA into a host cell.

The term "complementary strand," describes nucleic acid sequences or molecules in which each base in one molecule is paired with its complementary base in the other strand, to form a stable helical double strand molecule. The individual strands are termed complementary strands.

The term "oligonucleotide primer," is a sequence of linear oligonucleotides of about ten to about fifty nucleotides in length that are complementary to nucleotide sequences 5' or 3' to be amplified. A pair of oligonucleotide primers, in which one of the primers is complementary to a nucleotide sequence 5' of the polynucleotide fragment to be amplified while the other primer of the pair is complementary to a nucleotide sequence located 3' polynucleotide fragment to be amplified can be used to amplify a polynucleotide sequence. One skilled in the art understands that a pair of oligonucleotide primers means two oligonucleotides complementary to opposite strands of nucleic acid and flanking the polynucleotide sequence to be amplified.

The term "adapter," describes a short, oligonucleotide polynucleotide segment that can be joined to a polynucleotide molecule at either a blunt end or cohesive end. Adapters may contain restriction enzyme recognition sequences within the polynucleotide fragment. The size of the adapter can vary from about ten to about one-hundred and fifty nucleotides in length. Adapters can either be single stranded or double stranded.

The term "ligated isolated complementary strand," refers to a polynucleotide fragment which comprises an adapter joined to a second DNA fragment that contains a portion or all of the known polynucleotide sequence and an adjacent unknown polynucleotide sequence via a ligation reaction. A "ligated isolated complementary strand" is flanked by an adapter on one end and a known polynucleotide sequence on the other end.

A ligation reaction is completed by an enzyme, generally referred to as a ligase that catalyzes the formation of a phosphodiester bond between adjacent 3'-OH and 5'-P termini in DNA.

Isolation of a plant DNA can be accomplished by methods known in the art. Generally, the isolation of a plant DNA results in obtaining purified plant DNA which is free of lipids, proteins and other cellular debris. Preferred plant DNA isolation methods include: lysis, heating, alcohol precipitation, salt precipitation, organic extraction, solid phase extraction, silica gel membrane extraction, CsCl gradient purification, and any combinations thereof. A more preferred plant DNA isolation method is the silica-gel-membrane technology marketed as the DNeasy kit (Qiagen, Valencia, Calif.) or the Cetyltrimethylammonium Bromide (CTAB) DNA isolation protocol.

Restriction enzyme digestions, also referenced as restriction endonuclease digestions, are performed when a nuclease enzyme is used to cleave the polynucleotide sequences. There are numerous restriction enzymes available to those skilled in the art. As described at www.neb.com/nebecomm/tech_reference/restriction_enzymes/overview.asp, four classifications are used to characterize restriction enzymes. These classifications are made on the basis of subunit composition, cleavage position, sequence specificity and cofactor requirements.

Type I enzymes randomly cut DNA at locations which are a distance from the recognition/binding sequence (>1,000 bp away). The recognition sites which are bound by a Type I enzyme are asymmetrical. As a result these enzymes are not used for gene cloning because these enzymes do not produce discrete restriction fragments or distinct gel-banding patterns. Type I enzymes are multifunctional and the different subunits which comprise a Type I restriction enzyme are responsible for different activities (i.e. subunit HsdR encodes restriction, subunit HsdM encodes methylation of DNA, and subunit HsdS encodes specificity of the recognition sequence).

Type II enzymes digest DNA at positions located within close proximity of the recognition sequences. These enzymes function as a dimer, wherein a subunit binds to the sense strand and a second copy of the subunit binds to the antisense strand at a palindromic sequence which is typically between 4-8 nucleotides in length. The Type II dimer that binds to the DNA can be either a homodimer which bind to symmetric DNA sequences, or a heterodimer which binds to asymmetric DNA sequences. The enzymes can recognize either continuous sequences or discontinuous sequences. Type II enzymes are commercially available and commonly used for DNA analysis and gene cloning. Widespread usage of these enzymes is a result of distinct restriction fragments which are produced and can be resolved on an agarose gel.

Type II enzymes are a collection of unrelated proteins which are highly divergent in amino acid sequence similarity. Type II enzymes have been divided into subcategories which are labeled using a letter suffix. Type IIB restriction enzymes are multimers that contain more than one subunit. These enzymes cut both sides of the recognition sequence, thereby resulting in removal of the recognition sequence. Type IIE and Type IIF restriction enzymes cleave DNA following interaction with two copies of their recognition sequence. Type IIG restriction enzymes are comprised of a single subunit. The N-terminal portion of the enzyme possesses a DNA cleavage domain and DNA modification domain. The C-terminal portion of the enzyme possesses a DNA sequence binding domain. These enzymes cleave outside of their recognition sequence. Type IIM restriction enzymes recognize and cut methylated DNA. Type IIS restriction enzymes function as a dimer and cleave DNA at a location which is outside of the non-palindromic asymmetric recognition sites. These enzymes are comprised of two distinct domains, one for DNA binding and the other for DNA cleavage.

Type III enzymes are combination restriction-and-modification enzymes. These enzymes recognize two separate non-palindromic sequences and cleave outside of their recognition sequences. Type III enzymes require two recognition sequences in opposite orientations within the same DNA molecule to accomplish cleavage.

Type IV enzymes recognize methylated DNA. Examples include the McrBC and Mrr systems of *E. coli*.

Other methods are known in the art for cleaving polynucleotides and can be used in place of digesting the polynucleotide with a restriction enzyme, any of the group consisting of: lysis, a sequence-specific cleavage agent, non-sequence specific cleavage agent, sonication, shear-stress. French press, UV radiation, ionizing radiation, and DNase. In addition, to the restriction enzymes described above, homing endonucleases or Flap endonucleases or any combination of these enzymes could be used to digest the isolated DNA. A preferred method for digesting isolated plant DNA is the use of a TypeII restriction enzyme which is known to cut outside of the transgene sequence being transformed into the plant. Another preferred method for digesting isolated plant DNA is the use of a TypeII restriction enzyme which is known to cut at a site which is in close proximity of the end of the transgene sequence.

Primer extension reactions are used to produce a DNA or RNA strand which contains a known polynucleotide sequence and an unknown adjacent polynucleotide sequence. Primer extension methodologies result in the production of a complementary strand of DNA or RNA which contains the unknown polynucleotide sequence. The complementary strand of DNA or RNA is produced by a polymerase which extends along a template strand of DNA or RNA after complexing with an oligonucleotide primer which has bound to the known template strand of DNA or RNA. The oligonucleotide primer is designed to specifically bind to the known DNA or RNA sequence within the template strand of DNA or RNA. Numerous types of polymerase are commercially available for the extension reaction; T4 polymerase, TAQ polymerase, PFU polymerase, or Reverse Transcriptase are a few non-limiting examples of commonly used polymerases. Each polymerase has special buffer requirements and function at a specific temperature for optimal reaction conditions. A preferred primer extension reaction is the use of the TAQ polymerase marketed as the Platinum Taq kit.

Attachment chemistries attached to an isolation matrix such, as magnetic bead-based systems, are used to isolate the single stranded DNA produce by the primer extension reaction. The DNA strand which is produced by the primer amplification reaction can be purified from genomic DNA via a streptavidin-biotin interaction. Biotinylation is widely used to enable isolation, separation, concentration and further downstream processing and analysis of biomolecules (for example, methods described in U.S. Pat. No. 5,948,624, U.S. Pat. No. 5,972,693, and U.S. Pat. No. 5,512,439). There are a variety of commercially available biotinylation reagents that target different functional groups like primary amines, sulfhydryls, carboxyls, carbohydrates, tyrosine and histidine side chains and cyianidine and cytosine bases. The use of short, sequence-specific oligonucleotide primers functionalized with biotin (or the equivalent, e.g. digoxigenin) and magnetic beads to separate specific DNA sequences from the genome for subsequent analysis have multiple uses. Isolation using the bead-based method allows for enrichment of a population of DNA for a particular sequence, allowing subsequent analysis to be carried out that could not be done in the presence of the entire genomic complement of DNA. Such bead-based methods are suited for high throughput automation.

Although the biotin-streptavidin interaction is the best described binding pair, other molecules which have a strong affinity for one another are known. Attachment chemistries that can be included into a oligonucleotide primer include: ACRYDITE™ an attachment chemistry based on an acrylic phosphoramidite that can be added to oligonucleotides as a 5'-modification, and covalently reacts with thiol-modified surfaces; Alkyne modifications which react with azide labeled functional groups to form stable bonds through the azide alkyne Huisgen cycloaddition reaction (also referenced as the Click reaction); and, Thiol modifications which can couple and interact with high affinity to a corresponding ligand or surface (such as a gold surface). These molecules can be used for purification or enrichment of DNA sequences. Wherein, a primer is labeled with a first molecule and the second molecule is bound to a matrix which can immobilize the first molecule (e.g. magnetic beads). A DNA strand produced from the primer labeled with the first molecule can be isolated by running the DNA over a column containing the immobilized matrix (e.g. magnetic beads) labeled with the second molecule. As a result of the affinity for the second molecule, the amplified DNA sequences containing the primer labeled with the first molecule are isolated. Preferred attachment chemistries include acrylic-thiol interactions, alkyne-azide interactions, and thiol-ligand interactions. A, more preferred attachment chemistry is the streptavidin-biotin interaction.

As used herein, the term isolation matrix refers to a surface to which a molecule of any sort may be attached. Preferably, an isolation matrix is an insoluble material to which a molecule may be attached so that said molecule may be readily separated from other components in a reaction. Preferred isolation matrices may include, but is not limited to, a filter, a chromatography resin, a bead, a magnetic particle, or compositions that comprise glass, plastic, metal, one or more polymers and combinations thereof. A more preferred isolation matrix is the magnetic bead-based system.

Adapters can be ligated to an immobilized single stranded DNA via a single stranded ligase. Traditionally, commercially available ligases were only available for joining double stranded DNA fragments. Recently, it has been shown that an RNA ligase can be used to ligate single stranded DNA fragments (Zhang and Chiang (1995) Nucleic Acids Research, 24(5); 990-991). Preferred single stranded ligases are commercially available and marketed as CIRCLIGASE™ (Epicentre Biotechnologies, Madison, Wis.), T4 RNA ligase 1 and T4 RNA Ligase2 (New England Biolabs, Ipswich, Mass.), and Single Strand DNA Ligase (Wako Chemicals, Richmond, Va.). A more preferred single stranded DNA ligase is the Thermostable RNA Ligase (TRL) from Epicentre Biotechnologies (Madison, Wis.).

As described by Brautigma et al., 2010, DNA sequence analysis can be used to determine the nucleotide sequence of the isolated and amplified fragment. The amplified fragments can be isolated and sub-cloned into a vector and sequenced using chain-terminator method (also referred to as Sanger sequencing) or Dye-terminator sequencing. In addition, the amplicon can be sequenced with Next Generation Sequencing. NGS technologies do not require the sub-cloning step, and multiple sequencing reads can be completed in a single reaction. Three NGS platforms are commercially available, the Genome Sequencer FLX from 454 Life Sciences/Roche, the Illumina Genome Analyser from Solexa and Applied Biosystems' SOLiD (acronym for: 'Sequencing by Oligo Ligation and Detection'). In addition, there are two single molecule sequencing methods that are currently being developed. These include the true Single Molecule Sequencing (tSMS) from Helicos Bioscience and the Single Molecule Real Time sequencing (SMRT) from Pacific Biosciences.

The Genome Sequencer FLX which is marketed by 454 Life Sciences/Roche is a long read NGS, which uses emulsion PCR and pyrosequencing to generate sequencing reads. DNA fragments of 300-800 bp or libraries containing fragments of 3-20 kbp can be used. The reactions can produce over a million reads of about 250 to 400 bases per run for a total yield of 250 to 400 megabases. This technology produces the longest reads but the total sequence output per run is low compared to other NGS technologies.

The Illumina Genome Analyser which is marketed by Solexa is a short read NGS which uses sequencing by synthesis approach with fluorescent dye-labeled reversible terminator nucleotides and is based on solid-phase bridge PCR. Construction of paired end sequencing libraries containing DNA fragments of up to 10 kb can be used. The reactions produce over 100 million short reads that are 35-76 bases in length. This data can produce from 3-6 gigabases per run.

The Sequencing by Oligo Ligation and Detection (SOLiD) system marketed by Applied Biosystems is a short read technology. This NGS technology uses fragmented double stranded DNA that are up to 10 kbp in length. The system uses sequencing by ligation of dye-labelled oligonucleotide primers and emulsion PCR to generate one billion short reads that result in a total sequence output of up to 30 gigabases per run.

tSMS of Helicos Bioscience and SMRT of Pacific Biosciences apply a different approach which uses single DNA molecules for the sequence reactions. The tSMS Helicos system produces up to 800 million short reads that result in 21 gigabases per run. These reactions are completed using fluorescent dye-labelled virtual terminator nucleotides that are described as a 'sequencing by synthesis' approach.

The SMRT Next Generation Sequencing system marketed by Pacific Biosciences uses a real time sequencing by synthesis. This technology can produce reads of up to 1000 bp in length as a result of not being limited by reversible terminators. Raw read throughput that is equivalent to one-fold coverage of a diploid human genome can be produced per day using this technology.

The following examples describe a method developed to isolate and identify the genomic flanking sequences of a transgene insert. In addition, the method can be used to determine the transgene copy number and the genomic location of a transgene for a transgenic event.

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims. The disclosure of each reference set forth herein is incorporated herein by reference in its entirety.

EXAMPLE 1

A plasmid containing a gene of interest expression cassette and a selectable marker gene expression cassette was used to transform *Zea mays* cv Hi-II plant tissue via the Biorad gene gun. Production of transgenic maize from bombarded Type II callus: effect of gold particle size and callus morphology on transformation efficiency. *In Vitro Cell. Dev. Biol-Plant.* 36:21-29). The protocol was modified: media components, selection agents and timing were optimized to improve the efficiency of the transformation process. An Fsp I linearized fragment of the plasmid was used for the transformation. The resulting transformations produced transgenic maize plants which contained a gene of interest expression cassette which was linked to the plant selectable marker gene expression cassette.

EXAMPLE 2

Genomic DNA was isolated from three different maize events (3)-001, (3)-008, and (3)-009 and untransformed maize controls. Several methods were employed to isolate the gDNA, such as the DNeasy kit (Qiagen, Valencia, Calif.) or the traditional CTAB DNA isolation protocol. The DNA concentrations were determined using a Nanodrop (Thermo Scientific, Wilmington, Del.). A total of 250 ng of gDNA was digested with TaqI restriction enzyme. The digestion reaction was further purified using the MinElute Reaction Cleanup Kit (Qiagen, Valencia, Calif.).

EXAMPLE 3

Primer extension reactions using the isolated and purified gDNA were completed. A dual-biotin labeled primer was synthesized by Integrated DNA Technologies Inc. (Coralville, Iowa) and used for the reaction (SEQ ID NO:1 (4468-3PA01-2Btn) 5'-\Dual Biotin\-GGACAGAGCCACAAA-CACCACAAGA-3'). The Platinum Taq kit (Invitrogen, Carlsbad, Calif.) was used to synthesize a DNA strand via primer extension. The following reagents: 2 µL, 10× platinum TAQ buffer; 1.25 µL, 50 mM $MgCl_2$; 0.8 µL, 10 mM dNTP; 0.1 µL, 10 µM 4468-3PA01-2Btn; 0.1 µL Platinum TAQ; 14.75 µL $H_2O$; 1 µL gDNA were mixed in a tube. Amplification was completed using the following reaction conditions: 1) 94° C. 3 minutes; 2) 98° C. 10 seconds; 3) 63° C. 1 minute; 4) 72° C. 5 minutes; 5) repeat steps 2-4 15 times; 6) 72° C. 3 minutes; 7) 4° C. hold.

EXAMPLE 4

A capture reaction was completed with 2.5 µL of Dynabeads M-280 streptavidin magnetic beads (Invitrogen, Carlsbad, Calif.). The beads were washed on a magnet with PBST buffer (phosphate buffered saline and tween 20) one time and PBS buffer (phosphate buffered saline) two times. After the supernatant had been removed from the magnet, 20 µL, of PBS was added to the beads and the beads were mixed and resuspended. This solution was added to the single-primer extension reaction at a 1:1 concentration, 20 µL of beads were mixed with 20 µL of primer extension reaction. The resulting solution was incubated for 1 hour with gentle pipetting at room temperature. The beads were then washed over a magnet with PBST two times, PBS two times, and $H_2O$ one time. All of the wash solutions were removed from the beads.

EXAMPLE 5

A single stranded adapter was ligated to the single stranded captured target gDNA from events (3)-001, (3)-008, and (3)-009. The single stranded adaptor (SEQ ID NO:2 (ZC-Adp-01) 5'-/5Phos/ATTGGATTCTCTGACGGTCGGACGC/36-FAM/-3'), which was synthesized at Integrated DNA Technologies (Coralville, Iowa), was ligated with Thermostable RNA Ligase (TRL) from Epicentre Technologies (Madison, Wis.). The following reaction was used to ligate the adapter to the single stranded DNA: 0.125 µL of 100 uM ZC-Adp-01; 5.0 µL, of 50% PEG 8000 (W/V in $H_2O$); 1.0 µL of DMSO; and 1.875 µL of $H_2O$. The cocktail was mixed and denatured in a thermocycler at 94° C. for 5 minutes then cooled to room temperature. Then, 1 µL of 10×TRL buffer, 0.5 µL of 1 mM ATP, and of TRL were added and mixed into the solution. The resulting solution was added to the washed beads from the capture reaction and incubated on a thermocycler at 60° C. for 1 hour and then at 4° C. The beads were washed on a magnet with 0.1×TE buffer several times, and all liquid was removed from the beads.

EXAMPLE 6

PCR reactions were completed using the Takara LA TAQ HS PCR kit (Millipore, Billerica, Ma). The following primers were used to amplify the event and flanking sequence: Transgene specific primer, SEQ ID NO:3 (PAT-InvPriF) 5'-CGCT-TACGATTGGACAGTTGAGAGTACTG-3') and Adaptor primer, SEQ ID NO:4 (Zn_Adt_PCR_01) 5'-GTCCGAC-CGTCAGAGAATCCAAT-3'). The following reagents were used in the PCR reaction: 5 µL, 10× LA TAQ HS buffer; 8 µL, 2.5 mM dNTP, 1 µL 10 µM transgene specific primer; 1 µL, 10 µM adapter specific primer; 0.5 µL, LA Taq HS polymerase; and, 34.5 µL, $H_2O$. The cocktail was added to the washed beads from the ligation reaction and amplified using the following conditions in Table 1.

TABLE 1

| PCR amplification conditions | |
|---|---|
| 1 cycle | 94° C., 2 min |
| 2 cycles | 98° C., 10 sec |
| | 66° C., 1 min |
| | 68° C., 5 min |
| 28 cycles | 98° C., 10 sec |
| | 64° C., 30 sec |
| | 68° C., 2.5 min |
| 1 cycle | 72° C., 4 min |
| 1 cycle | 4° C., ∞ |

EXAMPLE 7

The resulting PCR products, of sizes greater than ~850 bp, were cloned into plasmid pCR2.1 (Invitrogen, Carlsbad, Calif.). Colonies were isolated and the pCR2.1 plasmid was confirmed to contain a PCR amplicon. The vectors were sequenced using M13 Forward and M13 Reverse primers. The sequencing results were expected to contain the nucleotide sequence of the maize 3'genomic flanking sequence in addition to the genetic elements present from the plasmid. The 3' transgene insert and maize genomic flanking sequences from events (3)-001 clone #4, (3)-008 clone #10, (3)-008 clone #13, and (3)-009 were isolated and identified using the technique described above.

The characterization of the genomic insertions indicated that event (3)-001 contains multiple copies of the transgene. Several unique inserts were identified within this event. Event (3)-001 clone #4 possesses a unique flanking region, in addition flanking sequences of a second and third insert which were rearranged were isolated (data not disclosed). The unique flanking regions indicate that three copies of the transgene inserted into unique locations of the *Zea mays* genome.

Event (3)-008 contains two copies of the transgene. The flanking sequences of Event (3)-008 clone #10 and (3)-008 clone #13 are unique and dissimilar, thereby indicating that two copies of the transgene inserted into unique locations of the *Zea mays* genome.

Event (3)-009 only contains one copy of the transgene. The isolated flanking region was used to identify the chromosomal location of the transgene insert within the *Zea mays* genome.

The identified maize genomic flanking sequences were BLASTED against The Maize Genome Sequencing Consortium, *Zea mays* B73 genomic database (Arizona Genomics Institute, University of Arizona) to identify the chromosomal location of the transgene insert. The flanking sequence of Event (3)-008 clone #13 was mapped to chromosome #5. The flanking sequence of Event (3)-009 was mapped to chromosome #3.

What is claimed is:

1. A method for finding an unknown polynucleotide sequence adjacent to a known polynucleotide sequence in isolated DNA, which comprises:
   a) digesting the isolated DNA that contains a portion or all of the known polynucleotide sequence and an adjacent unknown polynucleotide sequence with one or more suitable restriction enzymes to produce a plurality of digested polynucleotide restriction fragments;
   b) synthesizing a complementary strand of the digested polynucleotide restriction fragments using an oligonucleotide primer sequence having an attachment chemistry bound to the 5' end of the oligonucleotide primer sequence;
   c) isolating the complementary strand by binding the attachment chemistry to a suitable isolation matrix, then denaturing the complementary strand from the digested polynucleotide restriction fragments;
   d) ligating a single stranded adapter to the isolated complementary strand bound to the isolation matrix to produce a ligated isolated complementary strand, wherein said single stranded adaptor comprises SEQ ID NO: 2;
   e) performing a first PCR amplification of the ligated isolated complementary strand using a first PCR primer designed to bind to the known polynucleotide sequence and a second PCR primer designed to bind to the single stranded adaptor to produce a first PCR amplicon;
   f) performing a second PCR amplification of said first PCR amplicon, wherein the second PCR amplification amplifies an internal sequence of said first PCR amplicon to produce a second PCR amplicon; and,
   g) sequencing the second PCR amplicon to ascertain the sequence of the unknown polynucleotide sequence.

2. The method of claim 1, wherein the isolated DNA is plant genomic DNA.

3. The method of claim 1, wherein the unknown polynucleotide sequence is a transgene border sequence.

4. The method of claim 1, wherein the unknown polynucleotide sequence is a chromosomal sequence which flanks a known polynucleotide sequence.

5. The method of claim 1, wherein the unknown polynucleotide sequence is a native gene sequence which encodes a trait.

6. The method of claim 1, wherein the known polynucleotide sequence is a known polynucleotide viral sequence.

7. The method of claim 1 wherein the known polynucleotide sequence is a known polynucleotide transgene sequence.

8. The method of claim 1, wherein the known polynucleotide sequence is a known polynucleotide transposon sequence.

9. The method of claim 1, wherein the known polynucleotide sequence is a gene sequence that encodes a trait.

10. The method of claim 1, wherein the method is used to identify the chromosomal location of a known polynucleotide sequence inserted into the isolated plant DNA via insertion mutagenesis.

11. The method of claim 10, wherein said insertion mutagenesis is selected from the group consisting of transposon mutagenesis, or T-strand integration mutagenesis.

12. The method of claim 1, wherein the method is used to characterize an unknown polynucleotide sequence consisting of a chromosomal sequence which flanks a known polynucleotide sequence.

13. The method of claim 12, wherein said characterization of a transgene insertion site identifies a polynucleotide sequence consisting of rearrangements, insertions, deletions, or inversions within the unknown polynucleotide sequence consisting of a chromosomal sequence.

14. The method of claim 1, wherein the method is used to determine transgene copy number.

15. The method of claim 1, wherein the method is used to identify transgenic plant lines.

16. The method of claim 1, wherein the method is used to develop molecular marker systems.

17. The method of claim 1, wherein said one or more suitable restriction enzyme is TaqI.

18. The method of claim 1, wherein said single stranded adaptor is 5'-/5Phos/ATTGGATTCTCTGACGGTCGGACGC/36-FAM/-3' (SEQ ID NO: 2).

19. The method of claim 1, wherein said oligonucleotide primer comprises SEQ ID NO: 1.

20. The method of claim 19, wherein said oligonucleotide primer is 5'-\Dual Biotin\-GGACAGAGCCACAAACACCACAAGA-3' (SEQ ID NO: 1).

21. A method for finding an unknown polynucleotide to a known polynucleotide sequence in isolated DNA, which comprises:
   a) digesting the isolated DNA that contains a portion or all of the known polynucleotide sequence and an adjacent unknown polynucleotide sequence with one or more suitable restriction enzymes to produce a plurality of digested polynucleotide restriction fragments;
   b) synthesizing a complementary strand of the digested polynucleotide restriction fragments using an oligonucleotide primer sequence having an attachment chemistry bound to the 5' end of the oligonucleotide primer sequence;
   c) isolating the complementary strand by binding the attachment chemistry to a suitable isolation matrix, then denaturing the complementary strand from the digested polynucleotide restriction fragments;
   d) ligating a single stranded adapter to the isolated complementary strand bound to the isolation matrix to produce a ligated isolated complementary strand;
   e) performing a first PCR amplification of the ligated isolated complementary strand using a first PCR primer designed to bind to the known polynucleotide sequence and a second PCR primer designed to bind to the single stranded adaptor to produce a first PCR amplicon, wherein said first PCR primer comprises SEQ ID NO: 3 and said second PCR primer comprises SEQ ID NO: 4;
   f) performing a second PCR amplification of said first PCR amplicon, wherein the second PCR amplification amplifies an internal sequence of said first PCR amplicon to produce a second PCR amplicon; and
   g) sequencing the second PCR amplicon to ascertain the sequence of the unknown polynucleotide sequence.

22. The method of claim 21, wherein the isolated DNA is plant genomic DNA.

* * * * *

UNITED STATES PATENT AND TRADEMARK OFFICE
CERTIFICATE OF CORRECTION

| | | |
|---|---|---|
| PATENT NO. | : 8,911,943 B2 | Page 1 of 1 |
| APPLICATION NO. | : 13/439933 | |
| DATED | : December 16, 2014 | |
| INVENTOR(S) | : Cao et al. | |

It is certified that error appears in the above-identified patent and that said Letters Patent is hereby corrected as shown below:

In the specification

Column 1,
Lines 29-30, "identification or genomic" should read --identification of genomic--.

In the claims

Column 21,
Lines 21-22, claim 21 "polynucleotide to a known" should read
--polynucleotide sequence adjacent to a known--.

Signed and Sealed this
Thirteenth Day of October, 2015

Michelle K. Lee
*Director of the United States Patent and Trademark Office*

SEQUENCE LISTING

```
<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: 4468-3PA01-2Btn Primer

<400> SEQUENCE: 1
ggacagagcc acaaacacca caaga                                              25

<210> SEQ ID NO 2
<211> LENGTH: 25
<212> TYPE: DNA
<213> ORGANISM: Artificial Sequence
<220> FEATURE:
<223> OTHER INFORMATION: ZC-Adp-01 Adapter

<400> SEQUENCE: 2
attggattct ctgacggtcg gacgc                                              25

<210> SEQ ID NO 3
<211> LENGTH: 29
<212> TYPE: DNA
<213> ORGANISM: Artificial Sequence
<220> FEATURE:
<223> OTHER INFORMATION: PAT-InvPriF Primer

<400> SEQUENCE: 3
cgcttacgat tggacagttg agagtactg                                          29

<210> SEQ ID NO 4
<211> LENGTH: 23
<212> TYPE: DNA
<213> ORGANISM: Artificial Sequence
<220> FEATURE:
<223> OTHER INFORMATION: Zn_Adt_PCR_01 Primer

<400> SEQUENCE: 4
gtccgaccgt cagagaatcc aat                                                23

<210> SEQ ID NO 5
<211> LENGTH: 806
<212> TYPE: DNA
<213> ORGANISM: Artificial Sequence
<220> FEATURE:
<223> OTHER INFORMATION: pDAS102408 (3)-001 clone #4
<220> FEATURE:
<221> NAME/KEY: TransgeneSequence
<222> LOCATION: (1)..(728)
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: GenomicFlankingSequence
<222> LOCATION: (729)..(770)
```

<400> SEQUENCE: 5

```
gtgtgcgtga caccacgatg cctgtagcaa tggcaacaac gttgcgcaaa ctattaactg      60
gcgaactact tactctagct tcccggcanc aattaataga ctggatggag gcggataaag     120
ttgcaggacc acttctgcgc tcggcccttc cggctggctg gtttattgct gataaatctg     180
gagccggtga gcgtgggtct cgcggtatca ttgcagcact ggggccagat ggtaagccct     240
cccgtatcgt agttatctac acgacgggga gtcaggcaac tatggatgaa cgaaatagac     300
agatcgctga gataggtgcc tcactgatta agcattggta actgtcagac caagtttact     360
catatatact ttagattgat ttaaaacttc attttaatt taaaggatc taggtgaaga      420
tcctttttga taatctcatg accaaaatcc cttaacgtga gttttcgttc cactgagcgt     480
cagacccccgt agaaaagatc aaaggatctt cttgagatcc tttttttctg cgcgtaatct     540
gctgcttgca acaaaaaaa ccaccgctac cagcggtggt ttgtttgccg gatcaagagc     600
taccaactct ttttccgaag gtaactggct tcagcagagc gcagatacca atactgttc      660
ttctagtgta gccgtagtta ggccaccact tcaagaactc tgtagcaccg cctacatacc     720
tcgctctggg aaaaagagtt ggtagcaatt ggattctctg acggtcggac aagggcgaat     780
tccagcacac tggcggccgt tactag                                           806
```

<210> SEQ ID NO 6
<211> LENGTH: 836
<212> TYPE: DNA
<213> ORGANISM: Artificial Sequence
<220> FEATURE:
<223> OTHER INFORMATION: pDAS102408 (3)-008 clone #10
<220> FEATURE:
<221> NAME/KEY: TransgeneSequence
<222> LOCATION: (1)..(731)
<220> FEATURE:
<221> NAME/KEY: FlankingGenomicSequence
<222> LOCATION: (732)..(785)
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (826)..(826)
<223> OTHER INFORMATION: n is a, c, g, or t

<400> SEQUENCE: 6

```
tcggtcgcag cgtgtgcgtg tccgtcgtac gttctggccg gccgggcctt gggcgcgcga      60
tcagaaagcg ttgcgttggc gtgtgtgtgc ttctggtttg ctttaatttt accaagtttg     120
tttcaaggtg gatcgcgtgg tcaaggcccg tgtgctttaa agacccaccg gcactggcag     180
tgagtgttgc tgcttgtgta ggctttggta cgtatgggct ttatttgctt ctggatgttg     240
tgtactactt gggtttgttg aattattatg agcagttgcg tattgtaatt cagctgggct     300
acctggacat tgttatgtat taataaatgc tttgctttct tctaaagatc tttaagtgct     360
gaattcatat ttaaatcaat tcactggccg tcgttttaca acgtcgtgac tgggaaaacc     420
ctggcgttac ccaacttaat cgccttgcag cacatccccc tttcgccagc tggcgtaata     480
gcgaagaggc ccgcaccgat cgcccttccc aacagttgcg cagcctgaat ggcgaatggc     540
gcctgatgcg gtattttctc cttacgcatc tgtgcggtat ttcacaccgc atatggtgca     600
ctctcagtac aatctgctct gatgccgcat agttaagcca gccccgacac ccgccaacac     660
ccgctgacgc gccctgacgg gcttgtctgc tcccggcatc cgcttacaga caagctgtga     720
```

```
ccgtctccgg gtgttacttc tgcagggtac ccccgggggtc gaattggatt ctctgacggt      780
cggacaaggg cgaattccag cacactggcg gccgttacta gnggaaccga gctcgt            836
```

<210> SEQ ID NO 7
<211> LENGTH: 944
<212> TYPE: DNA
<213> ORGANISM: Artificial Sequence
<220> FEATURE:
<223> OTHER INFORMATION: pDAS102408 (3)-008 clone #13
<220> FEATURE:
<221> NAME/KEY: TransgenicSequence
<222> LOCATION: (153)..(587)
<220> FEATURE:
<221> NAME/KEY: FlankingGenomicSequence
<222> LOCATION: (588)..(908)

<400> SEQUENCE: 7

```
ttaagttggg taacgccagg gttttcccag tcacgacgtt gtaaaacgac ggccagtgaa        60
ttgtaatacg actcactata gggcgaattg ggccctctag atgcatgctc gagcggccgc       120
cagtgtgatg gatatctgca gaattcgccc ttcgcttacg attggacagt tgagagtact      180
gtttacgtgt cacataggca tcaaaggttg ggcctaggat ccacattgta cacacatttg      240
cttaagtcta tggaggcgca aggttttaag tctgtggttg ctgttatagg ccttccaaac      300
gatccatctg ttaggttgca tgaggctttg ggatacacag cccggggtac attgcgcgca      360
gctggataca agcatggtgg atggcatgat gttggttttt ggcaaaggga ttttgagttg      420
ccagctcctc caaggccagt taggccagtt acccagatct gaggtaccct gagctcggtc      480
gcagcgtgtg cgtgtccgtc gtacgttctg gccggccggg ccttgggcgc gcgatcagaa      540
gcgttgcgtt ggcgtgtgtg tgcttctggt ttgctttaat tttaccacgc cagccccgac      600
acccgccaac acccgctgac gcgccctgac gggcttgtct gctcccggca tccgcttaca      660
gacaagctgt gaccgtctcc gggagctgca tgtgtcagag gttttcaccg tcatcaccga      720
aacgcgcgag acgaaagggc ctcgtgatac gccccacatc atcacaacca agacaaaaaa      780
agcatgaaaa gatgacccga caaacaagtg cacggcatat attgaaataa aggaaaaggg      840
caaaccaaac cctatgcaac gaaacaaaaa aaatcatgaa atcgaattgg attctctgac     900
ggtcggacaa gggcgaattc cagcacactg gcggccgtta ctag                        944
```

<210> SEQ ID NO 8
<211> LENGTH: 1024
<212> TYPE: DNA
<213> ORGANISM: Artificial Sequence
<220> FEATURE:
<223> OTHER INFORMATION: pDAS102408 (3)-009
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: FlankingGenomicSequence
<222> LOCATION: (51)..(132)
<220> FEATURE:
<221> NAME/KEY: TransgenicSequence
<222> LOCATION: (133)..(839)
<220> FEATURE:
<221> NAME/KEY: misc_feature
<222> LOCATION: (982)..(982)
<223> OTHER INFORMATION: n is a, c, g, or t
<220> FEATURE:
<221> NAME/KEY: misc_feature
<222> LOCATION: (992)..(994)
<223> OTHER INFORMATION: n is a, c, g, or t

<400> SEQUENCE: 8

```
cgagctcgga tccnctagta acggccgcca gtgtgctgga attcgcccttgtccgaccgt     60 cagagaatcc aattcgagct cgtttaaact gagggcactg aagtcgcttg atgtgtatct   120
tggtatcgcg catgaaaagg tggcaaattt cctcagcact taaagatctt tagaagaaag   180
caaagcattt attaatacat aacaatgtcc aggtagccca gctgaattac aatacgcaac   240
tgctcataat aattcaacaa acccaagtag tacacaacat ccagaagcaa ataaagccca   300
tacgtaccaa agcctacaca agcagcaaca ctcactgcca gtgccggtgg gtctttaaag   360
cacacgggcc ttgaccacgc gatccacctt gaaacaaact tggtaaaatt aaagcaaacc   420
agaagcacac acacgccaac gcaacgcttc tgatcgcgcg cccaaggccc ggccggccag   480
aacgtacgac ggacacgcac acgctgcgac cgagctcagg gtacctcaga tctgggtaac   540
tggcctaact ggccttggag gagctggcaa ctcaaaatcc ctttgccaaa aaccaacatc   600
atgccatcca ccatgcttgt atccagctgc gcgcaatgta ccccgggctg tgtatcccaa   660
agcctcatgc aacctaacag atggatcgtt tggaaggcct ataacagcaa ccacagactt   720
aaaaccttgc gcctccatag acttaagcaa atgtgtgtac aatgtggatc ctaggcccaa   780
cctttgatgc ctatgtgaca cgtaaacagt actctcaact gtccaatcgt aagcgaaggg   840
cgaattctgc agatatccat cacactggcg gccgctcgag catgcatcta gagggcccaa   900
ttcgccctat agtgagtcgt attacaattc actgggccgt cgttttacaa cgtcgtgact   960
gggaaaaccc tggcgttacc cnacttaatc gnnngcagca catcccccttttcgcagctg  1020 gcgt                                                              1024
```